US00PP09961P

United States Patent [19]

Bradford et al.

[11] Patent Number: Plant 9,961

[45] Date of Patent: Jul. 15, 1997

[54] NECTARINE TREE 'FIRE SWEET'

[76] Inventors: Lowell Glen Bradford, 12439 E. Savana Rd.; Norman G. Bradford, 11875 E. Savana Rd., both of Le Grand, Calif. 95333

[21] Appl. No.: 647,104

[22] Filed: May 9, 1996

[51] Int. Cl.[6] ..... A01H 5/00

[52] U.S. Cl. ..... Plt./41.1

[58] Field of Search ..... Plt./41.1

[56] References Cited

U.S. PATENT DOCUMENTS

P.P. 6,363 11/1988 Bradford et al. ..... Plt./41.1
P.P. 7,506 4/1991 Bradford et al. ..... Plt./41.1
P.P. 8,461 11/1993 Bradford et al. ..... Plt./40.1

*Primary Examiner*—James R. Feyrer

[57] ABSTRACT

The present invention relates to a nectarine, *Prunus persica* tree and more particularly to a new and distinct variety broadly characterized by a large size, vigorous, productive and regular bearing tree. The fruit matures under the ecological conditions described approximately the last week in July, with first picking on Jul. 24, 1995. The fruit is uniformly large in size, subacidic in flavor, globose in shape, clingstone in type, very firm in texture, and nearly full red in skin color. The variety was a first generation cross using Summer Fire (U.S. Plant Pat. No. 7,506) yellow flesh nectarine as the selected seed parent and an unnamed white flesh nectarine seedling as the selected pollen parent, which was previously developed by crossing August Red (U.S. Plant Pat. No. 6,363) nectarine by Bradcrim (U.S. Plant Pat. No. 8,461) nectarine.

1 Drawing Sheet

BACKGROUND OF THE VARIETY

In a continuing effort to improve the quality of fresh market and shipping fruit, we, the inventors, typically hybridize a large number of nectarine and peach seedlings each year. The present invention relates to a new and distinct variety of nectarine tree, which has been denominated varietally as "Fire Sweet". The present variety was developed by us in 1991 in a cultivated area of our experimental orchard at Bradford Farms near Le Grand, Calif. in Merced County (San Joaquin Valley). It was a first generation cross using Summer Fire (U.S. Plant Pat. No. 7,506) nectarine as the seed parent and an unnamed white flesh nectarine seedling as the selected pollen parent. This unnamed pollen parent was previously developed by crossing August Red (U.S. Plant Pat. No. 6,363) nectarine by Bradcrim (U.S. Plant Pat. No. 8,461) nectarine. Subsequent to origination of the present variety of nectarine tree, we asexually reproduced it by budding and grafting, and such reproduction of plant and fruit characteristics were true to the original plant in all respects.

The present variety is most similar to its seed parent, the Summer Fire (U.S. Plant Pat. No. 7,506), by producing yellow flesh clingstone nectarines that are nearly full red in skin color and very firm in texture, but is distinguished therefrom and an improvement thereon by producing fruit that is subacidic rather than acidic in flavor, that ripens about 6 days later, that is more globose in shape, and that has a bitter kernel instead of sweet.

The present variety is smaller to Bradcrim (U.S. Plant Pat. No. 8,461), one pollen grandparent, by producing nectarines that are full red in skin color and subacidic in flavor, but is very distinguished therefrom by producing fruit that is yellow flesh instead of white flesh, that is clingstone instead of freestone, that is much firmer, and that ripens about 30 days later. The present variety is similar to August Red (U.S. Plant Pat. No. 6,363), the other pollen grandparent, by producing yellow flesh clingstone nectarines that are large and very firm in texture, but is very distinguished therefrom by producing fruit that is subacidic in flavor instead of acidic, that is much sweeter, and that ripens about 20 days earlier.

DRAWING

The accompanying photograph exhibits four whole fruits positioned to display the charcteristics of the skin color and form, a sectioned fruit divided transverse to the suture plane to reveal the flesh, a typical stone, and representative leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of hard eating ripe on Aug. 1, 1995. All major color code designations are by reference to the Inter-Society Color Council, National Bureau of Standards. Common color names are also used occasionally.

TREE

Size: Medium.
Vigor: Medium.
Growth: Spreading and dense.
Form: Round topped.
Hardiness: Hardy.
Production: Productive.
Bearing: Regular bearer.
Trunk:
- *Size.*—Medium.
- *Texture.*—Medium.
- *Bark color.*—Grayish yellowish brown [80. gy.yBr].
- *Lenticels.*—Numerous. Color: Grayish brown [61. gy.Br]. Average size: ¼" [6.4 mm.].

Branches:
- *Size.*—Medium.
- *Texture.*—Medium.
- *Color.*—1st year wood topside: Light grayish red [18. l.yg.R]. 1st year wood underside: Brilliant yellow green [116. brill.YG]. Older wood: Light brown [57. l.Br].
- *Lenticels.*—Numerous, small. Color: Deep orange yellow [69. deep OY]. Average size: 1/16" [1.6 mm.].

Leaves:
*Size.*—Large. Average length: 6½" [165.1 mm.]. Average width: 1¾" [44.5 mm.].
*Thickness.*—Medium.
*Form.*—Elliptical.
*Apex.*—Acuminate.
*Base.*—Acute.
*Surface.*—Smooth.
*Color.*—Dorsal surface: Moderate olive green [125. m.OlG]. Ventral surface: Moderate yellow green [120. m.YG].
*Margin.*—Finely serrate.
*Venation.*—Pinnately net veined.
*Petiole.*—Average length: ½" [12.7 mm.]. Average thickness: 1/16" [1.6 mm.]. Color: Moderate yellow green [120. m.YG].
*Stipules.*—Numerous. Average length: ¼" [6.4 mm.].
*Glands.*—Average number: 2 to 4 per leaf. Position: Oppositely positioned on petiole and base of blade. Size: Medium. Form: Reniform. Color: Light yellow green [119. l.YG].

Flower buds:
*Hardiness.*—Hardy.
*Size.*—Medium.
*Length.*—Medium.
*Form.*—Free.
*Surface.*—Pubescent.

Flowers:
*Blooming period.*—Late as compared with other varieties.
*Size.*—Small.
*Color.*—Moderate purplish red [258. m.pR].

FRUIT

Maturity when described: Firm eating ripe, Aug. 1, 1995.
Date of first picking: Jul. 24, 1995.
Date of last picking: Aug. 8, 1995.
Size: Uniform, medium.
*Average diameter axially.*—2 13/16" [71.4 mm.].
*Average transversely in suture plane.*—2 11/16" [68.3 mm.].
Form: Uniform, globose to slightly oblong, symmetrical.
*Longitudinal section form.*—Round to oval.
*Transverse section through diameter.*—Round.
Suture: A shallow groove extending from the base to beyond the apex, having a slight depression beyond the pistil point.
Ventral surface: Rounded, lipped toward the apex on both sides.
Lips: Mostly equal, but a few unequal.
Cavity: Flaring, elongated in the suture plane, suture showing on one side, stem markings typically present.
*Depth.*—7/16" [11.1 mm.].
*Breadth.*—⅞" [22.2 mm.].
Base: Rounded, but cuneate when viewed along the suture plane.
Apex: Rounded to somewhat depressed.
Pistil point: Negligible in length, apical, depressed within the suture.
Stem: Medium.
*Average length.*—⅜" [9.5 mm.].
*Average width.*—3/16" [4.8 mm.].
Skin:
*Thickness.*—Medium.
*Texture.*—Medium.
*Tenacity.*—Tenacious to flesh.
*Tendency to crack.*—None observed.
*Color.*—Dark red [16. d.R] over a moderate reddish orange [37. m.rO] background with some pale orange yellow [73. p.OY] freckling near the apex.

Flesh:
*Color.*—Brilliant yellow [83. brill.Y] toward the skin with some slight dark red [16. d.R] streaking very close to the stone.
*Amygdalin.*—Scarce.
*Juice.*—Abundant, rich.
*Texture.*—Firm, tough, very crisp.
*Fibers.*—Abundant, fine.
*Ripens.*—Evenly.
*Flavor.*—Subacidic and very sweet with 16 to 18 brix.
*Aroma.*—Slight.
*Eating quality.*—Very best.

STONE

Type: Clingstone.
Form: Oval.
Base: Slightly oblique.
Apex: Rounded to slightly acute.
Sides: Equal.
Surface: Pitting toward the base, irregularly furrowed toward the apex.
Ridges: Jagged toward the base.
Color: Dark yellowish brown [78. d.yBr].
Pit wall: ¼" [6.4 mm.] thick.
Tendency to split: None observed.
Kernel:
*Form.*—Oval.
*Taste.*—Bitter.
*Viable.*—Yes.
*Average width.*—½" [12.7 mm.].
*Average length.*—13/16" [20.6 mm.].
*Color.*—Deep orange yellow [69. deep OY] with moderate brown [58. m.Br] veins when dry.
*Pellicle color.*—Deep yellowish brown [75. deep yBr].
*Amygdalin.*—Abundant.

USE

Market: Fresh and long distance shipping.
Keeping quality: Excellent.
Shipping quality: Excellent.
Resistance to insects: No unusual susceptibilities noted.
Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, which is most similar to its seed parent, the Summer Fire (U.S. Plant Pat. No. 7,506), by producing yellow flesh clingstone nectarines that are nearly full red in skin color and very firm in texture, but is distinguished therefrom and an improvement thereon by producing fruit that is subacidic rather than acidic in flavor, that ripens about 6 days later, that is more globose in shape, and that has a bitter kernel instead of sweet.

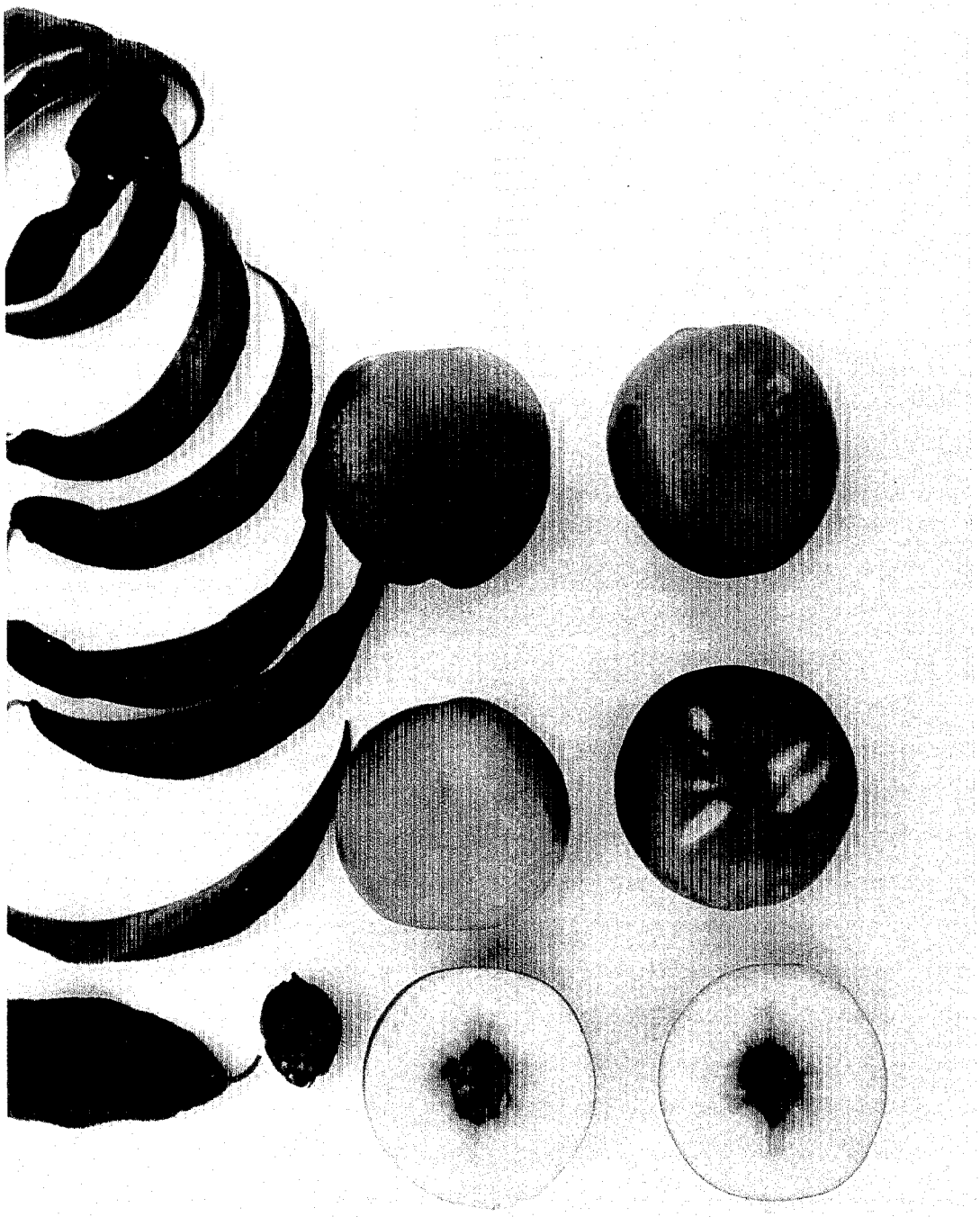

* * * * *